(12) United States Patent
Kochanczyk et al.

(10) Patent No.: US 10,011,861 B2
(45) Date of Patent: Jul. 3, 2018

(54) CLEAVABLE HAIRPIN PRIMERS

(71) Applicant: LUMINEX CORPORATION, Austin, TX (US)

(72) Inventors: Martin Kochanczyk, Austin, TX (US); Doug Whitman, Round Rock, TX (US)

(73) Assignee: LUMINEX CORPORATION, Austin, TX (US)

( * ) Notice: Subject to any disclaimer, the term of this patent is extended or adjusted under 35 U.S.C. 154(b) by 269 days.

(21) Appl. No.: 14/826,518

(22) Filed: Aug. 14, 2015

(65) Prior Publication Data

US 2016/0046995 A1 Feb. 18, 2016

Related U.S. Application Data

(60) Provisional application No. 62/037,315, filed on Aug. 14, 2014.

(51) Int. Cl.
*C12Q 1/68* (2018.01)
*C12Q 1/6827* (2018.01)

(52) U.S. Cl.
CPC .................. *C12Q 1/6827* (2013.01)

(58) Field of Classification Search
None
See application file for complete search history.

(56) References Cited

U.S. PATENT DOCUMENTS

| | | |
|---|---|---|
| 6,403,319 B1 | 6/2002 | Lizardi et al. |
| 7,056,671 B2 | 6/2006 | Enoki et al. |
| 2009/0068643 A1 | 3/2009 | Behlke et al. |
| 2010/0285473 A1 | 11/2010 | Wolff et al. |
| 2012/0258455 A1 | 10/2012 | Behlke et al. |
| 2013/0085078 A1 | 4/2013 | Schrader et al. |
| 2013/0210019 A1 | 8/2013 | Korfhage et al. |
| 2013/0288245 A1 | 10/2013 | Boyd |

FOREIGN PATENT DOCUMENTS

| | | |
|---|---|---|
| WO | WO 2011/008530 | 1/2011 |
| WO | WO 2013/142364 | 9/2013 |

OTHER PUBLICATIONS

Dobosy, et al., "RNase H-dependent PCR (rhPCR): improved specifically and single nucleotide polymorphism detection using blocked cleavable primers," *BMC Biotechnology*, 11:1-18, 2011.

Hou, et al., "A metion for HLA genotyping using the specific cleavage of DNA-rN$_1$-DNA/DNA with RNase HII from *Chlamydia pneumoniae*," *Oligonucleotides*, 17:433-443, 2007.

International Search Report and Written Opinion, issued in PCT/US2015/045242, dated Nov. 24, 2015.

*Primary Examiner* — David C Thomas
(74) *Attorney, Agent, or Firm* — Parker Highlander PLLC

(57) ABSTRACT

Nucleic acid constructs and methods that provide superior prevention of primer-dimers and other artifacts of false priming events are disclosed. In particular, there is disclosed a hairpin primer having a target-specific primer region, wherein the target-specific region comprises a target-binding dependent cleavage sequence; a first stem forming region 5' of the target-specific primer region; and a second stem forming region 3' of the target-specific primer region, wherein the second stem forming region is complementary to the first stem forming region. Methods of using the hairpin primer to amplify a target nucleic acid are also disclosed.

10 Claims, 2 Drawing Sheets

CLEAVABLE HAIRPIN PRIMERS

This application claims the benefit of U.S. Provisional Patent Application No. 62/037,315, filed Aug. 14, 2014, the entirety of which is incorporated herein by reference.

BACKGROUND OF THE INVENTION

1. Field of the Invention

The present invention relates generally to the fields of genetics and molecular biology. More particularly, it concerns the detection of nucleic acids.

2. Description of Related Art

Nucleic acid amplification and detection techniques are frequently employed in analyzing DNA samples for mutations and polymorphisms. They are also employed in the detection and typing of bacteria, viruses, and fungi, including those that are infectious pathogens, by analysis of their DNA or RNA. The most common form of nucleic acid amplification is the polymerase chain reaction (PCR), which uses short oligonucleotide sequences called primers to initiate the reaction at a specific site within the target genome. The specificity of the polymerase chain reaction is dependent upon hybridization of the primers to the target nucleic acid. Factors affecting this specificity include the melting temperature (Tm), which is the temperature at which one-half of a population of hybridized oligonucleotides will dissociate and become single stranded. Typically, a primer Tm is designed to be just above the annealing temperature set on the thermal cycling instrumentation, so that, ideally, only those target sequences which are perfectly complimentary to the primer sequences will anneal, and those which are not perfectly complimentary will not anneal. Often the temperature drops below the ideal annealing temperature, such as during PCR reactions, which include reverse transcription (RT) stages, or in the case of instrument to instrument temperature variation. These lower than ideal annealing temperatures can have adverse effects on the specificity of the PCR, allowing mis-priming events to unintended targets as well as primer-primer annealing, causing unintended amplification of primer-dimers which can out compete the intended target amplification.

Attempts have been made previously to limit the activity of the polymerase enzymes during the PCR set up and reverse transcription (RT) stages by using methods known as "hot-start." These methods are intended to reduce the formation of primer-dimers and other products of non-specific hybridization followed by extension. In these methods, a heat activation of polymerase is used to bring the polymerase to full activity. U.S. Pat. Nos. 5,773,258 5,677,152, and 5,338,671 incorporated herein by reference use either chemical modification, or antibody binding to reduce polymerase activity prior to heat induced cleavage of chemical modifications or heat induced denaturation of the inhibiting antibody. These methods are beneficial in reducing the polymerase activity dramatically, but are known to retain varying degrees of some polymerase activity, thereby not completely eliminating the problem. The reverse transcriptase enzyme itself can also exhibit some DNA polymerase activity, which can also lead to non-specific priming events. Other hot-start methods are known as "manual hot-start" and often include withholding one or more reagents from the reaction until a later stage. These manual methods are often labor intensive, or require automated liquid handling devices, and increase the risk of contamination of the PCR reaction.

Other attempts at reducing primer-dimers and other forms of non-specific amplification include the method of using linear (non-hairpin forming) primers comprising a cleavage domain within the target binding region as well as a blocking group at the 3' end of each primer. These methods also claim the use of a hotstart cleaving enzyme which is thermostable. Examples are described in US2012/0258455 and US2013/0288245, both of which are incorporated herein by reference. While these methods may provide some increased level of specificity, they suffer from the same drawbacks as other hot-start methods, in that some enzyme activity remains in these methods prior to heat activation.

Kaboev et. al. 2000, described using hairpin-like structured primers, to achieve an increase in specificity. This method is restrictive however in the practical design of PCR primer-based assays, in that the developer is limited to using natural target sequences for the oligonucleotide composition of the stem.

There remains a need to provide a method of priming and amplification that provides superior prevention of primer-dimers and other artifacts of false priming events, particularly when the reaction is exposed to lower than ideal annealing temperatures.

SUMMARY OF THE INVENTION

Various embodiments of the present invention provide nucleic acid constructs and methods that provide superior prevention of primer-dimers and other artifacts of false priming events.

In one embodiment, there is provided a nucleic acid construct comprising: (a) a target-specific primer region, wherein the target-specific region comprises a target-binding dependent cleavage sequence; (b) a first stem forming region 5' of the target-specific primer region; and (c) a second stem forming region 3' of the target-specific primer region, wherein the second stem forming region is complementary to the first stem forming region. The nucleic acid construct is configured such that it forms a hairpin structure under certain conditions. As such, the nucleic acid construct is also referred to herein as a "hairpin primer." In particular, the melt temperature (Tm) of the folded state of the hairpin primer, $Tm_{hairpin}$, is designed to be lower than the Tm of the target-specific region of the primer that is complementary to the target, $Tm_{specific}$. Thus, as the temperature is lowered from above $Tm_{specific}$ to below $Tm_{specific}$, unfolded hairpin primers anneal to target. Once annealed to the target, the target-binding dependent cleavage sequence can be recognized by a cleaving agent and cleaved. Cleavage results in (1) a released fragment containing the second stem forming region and a portion of the target-specific region that is 3' of the cleavage site, and (2) a primer fragment. The released fragment is designed to have a significantly lower melting temperature with the target sequence than the primer fragment, and therefore will not anneal to the target once it is cleaved, allowing extension to occur from the now available 3' end of the primer fragment. When the temperature is lowered below $Tm_{specific}$ and approaches $Tm_{hairpin}$, hairpin primers that did not anneal to the target, and therefore were not cleaved, fold into the hairpin state, making them unavailable for mispriming events. A person of skill in the art will be familiar with factors affecting nucleic acid hybridization, such as sequence length and G+C content, and will be able to determine the appropriate lengths for the stem regions, target-specific regions, the released fragment, and the primer fragment in a hairpin-forming nucleic acid molecule as described herein in order to achieve the properties mentioned above for a particular application.

The target-binding dependent cleavage sequence in the target-specific region is a sequence that is recognized by a cleaving agent when in a double-stranded state but is not recognized to a significant degree by the cleaving agent when in a single-stranded state. In the hairpin state of the nucleic acid constructs described herein, the target-specific region is single stranded and, therefore, it is not a substrate for the cleaving agent. When the nucleic acid construct is hybridized to a target nucleic acid, the target-binding dependent cleavage sequence is double stranded and, therefore, is a substrate for the cleaving agent.

There are a number of target-binding dependent cleavage sequences and cleaving agents that may be used. For example, in certain embodiments the target-binding dependent cleavage sequence may comprise one or more ribonucleotides and the cleaving agent may be an RNase, such as RNase H, RNase H2, RNase H2A, RNase H2B, and RNase H2C, and hotstart and/or thermophilic variants thereof. In certain aspects, the target-binding dependent cleavage sequence contains 1, 2, 3, 4, 5, or more ribonucleotides. Typically the ribonucleotide(s) should be placed no less than 3 bases away from the second stem forming region to allow for RNase H binding and cleavage. In certain embodiments, the ribonucleotide(s) are located between 3 to 12, 3 to 10, 3 to 8, 3 to 6, 4 to 12, 4 to 10, 4 to 8, or 4 to 6 bases away from the second stem forming region. As a further example, the target-binding dependent cleavage sequence may comprise sequence-specific nicking enzyme recognition sequence and the cleaving agent may be a sequence-specific nicking enzyme. Sequence-specific nicking enzymes hydrolyze only one strand of DNA, and they do so in a sequence-specific, strand-specific, and location-specific manner. Non-limiting examples of sequence-specific nicking enzymes include BbvCI and AlwI. Regardless of the target-binding dependent cleavage sequence employed, it should be positioned such that the cleavage of the nucleic acid construct results in the released fragment having a significantly lower melting temperature with the target sequence than the primer fragment.

The target nucleic acid sequence may be any sequence of interest. A sample may be any sample that contains, or is suspected of containing, nucleic acids. A sample may comprise DNA (e.g., genomic DNA), RNA (e.g., mRNA), and/or cDNA, any of which may be amplified to provide an amplified nucleic acid. In certain aspects of the invention the sample is, for example, a subject who is being screened for the presence or absence of one or more genetic mutations or polymorphisms. In another aspect of the invention the sample may be from a subject who is being tested for the presence or absence of a pathogen. Where the sample is obtained from a subject, it may be obtained by methods known to those in the art such as aspiration, biopsy, swabbing, venipuncture, spinal tap, fecal sample, or urine sample. In some aspects of the invention, the sample is an environmental sample such as a water, soil, or air sample. In other aspects of the invention, the sample is from a plant, bacteria, virus, fungi, protozoan, or metazoan.

As mentioned above, the first and second stem forming regions are configured to hybridize to each other at temperatures of $Tm_{hairpin}$ or lower, and to be single stranded at temperatures of $Tm_{specific}$ or above. In certain embodiments, the first and second stem forming regions are 5, 6, 7, 8, 9, 10, 11, 12, 13, 14, 15, or 16 nucleotides in length, or any range therein. The stem forming regions may comprise naturally occurring nucleotides, non-naturally occurring nucleotides, or a combination thereof. In certain embodiments, one of the first and second stem forming regions comprises an isoC and the other comprises an isoG at a position complementary to the isoC. In some embodiments, the first and second stem forming regions comprise a plurality of complementary isoC and isoG nucleotides. In certain aspects, $Tm_{hairpin}$ is between about 44° C. and 72° C., between about 45° C. and 65° C., between about 55° C. and 65° C. or between about 45° C. and 55° C. The $Tm_{hairpin}$ may be designed to be between the ideal primer annealing temperature of the instrument and the $Tm_{specific}$. For example, if the annealing temperature of the instrument was set at 58° C., the $Tm_{specific}$ could be designed near 63° C. and the $Tm_{hairpin}$ could be designed near 60° C.

In certain embodiments the stem region sequences are artificially designed. Such designs can be used as a universal stem in a multiplexed assay, further reducing the bioinformatic burden of avoiding cross-reactivity. Multiple types of assays can also benefit from using these pre-verified universal stem sequences. These artificial stem designs can also be enhanced by modifications using non-natural bases (see, e.g., U.S. Pat. Nos. 5,432,272, 6,977,161, and 7,422,850 all of which are incorporated herein by reference) that only bind with each other, as well as using sequences that have been bioinformatically derived to not cross-react with any sequences found in nature (see, e.g., U.S. Pat. Nos. 8,624, 014 and 7,226,737, both of which are incorporated herein by reference). It is typically the 3' end of the primer sequence that is most sensitive to non-specific amplification; therefore, avoiding risk of cross-reactivity by using artificial sequences in the stem forming regions can be advantageous.

In certain embodiments, the nucleic acid constructs disclosed herein further comprise a quencher incorporated into one of the first or second stem forming regions and a fluorophore incorporated into the other of the of the first or second stem forming regions. In particular embodiments, the fluorophore/quencher is incorporated at the 5' end of the first stem forming region and the 3' end of the second stem forming region. Incorporation of a fluorophore quencher pair can be used for, for example, facilitating the simultaneous priming and detection of the target nucleic acid.

The nucleic acid constructs may further comprise one or more polymerase extension blockers. In one embodiment, the nucleic acid construct comprises an extension blocker 5' of the target-specific primer region and 3' of the first stem forming region. By inserting an extension blocker in front of (i.e., 3' of) the first stem forming region the first stem forming region is not incorporated into the amplicon. This would create a 5' single-stranded region or "tag" at one end of the amplicon, if only one of a pair of nucleic acid constructs has the extension blocker, or on both ends of the amplicon if both nucleic acid constructs have the extension blocker. A tag could be used in a capture step or a probing step if the stems are unique to the amplicon. In some embodiments, the nucleic acid construct comprises an extension blocker at its 3' end. An extension blocker in this position would provide an additional layer of protection from the nucleic acid construct priming the synthesis of a polynucleotide prior to cleavage of the nucleic acid construct. The 3' hydroxyl group may be blocked with, for example, a phosphate group, a non-naturally occurring base that is not recognized by polymerase, or a 3' inverted dT. Other non-limiting examples of extension blockers that may be used in the template strand include C6-20 straight chain alkylenes, iSp18 (which is an 18-atom hexa-ethyleneglycol), iMe-isodC, a hexethylene glycol monomer, synthetic nucleic acid bases, 2-O-alkyl RNA, or an oligonucleotide sequence in the reverse orientation.

The nucleic acid constructs disclosed herein are particularly useful in multiplex PCR reactions because these constructs are configured such that they are closed (i.e., in a hairpin state), and thus unavailable for mispriming or primer-dimer formation at temperatures lower than the specific annealing temperature of the target-specific sequence to the target sequence, which significantly mitigates non-specific interactions, allowing for the plex for PCR assays to be increased. Thus, various embodiments provide mixtures of a plurality of nucleic acid constructs suitable for use in multiplex PCR. Furthermore, if desired, the same stem forming regions may be used for all hairpin primers in a multiplex PCR, thereby simplifying the hairpin primer design. For example, in one embodiment a composition is provided that comprises two or more populations of the nucleic acid constructs disclosed herein, wherein (i) the target-specific primer region of one population of nucleic acid constructs differs from the target-specific primer regions of the other populations of nucleic acid constructs, and (ii) the first and second stem forming regions are the same among the two or more populations nucleic acid constructs.

The nucleic acid constructs can be used in PCR, reverse transcription (RT), and RT-PCR. One embodiment provides a method for amplifying a target nucleic acid comprising: (a) contacting a sample with a first nucleic acid construct as disclosed herein and a second nucleic acid construct as disclosed herein, wherein the target-specific primer regions of said first and second nucleic acid constructs are configured as a primer pair for amplifying a target nucleic acid; (b) hybridizing the first and second nucleic acid constructs to the target nucleic acid if present in the sample; (c) cleaving the first and second nucleic acid constructs with a cleaving agent that recognizes the target-binding dependent cleavage sequences of the first and second nucleic acid constructs to obtain first and second extendable primers; and (d) extending the first and second extendable primers to amplify the target nucleic acid.

As mentioned above, the nucleic acid constructs disclosed herein are particularly useful in multiplexed reactions. The methods disclosed herein provide multiplexing capabilities such that a plurality of primer pairs may amplify a plurality of target nucleic acids in a single PCR reaction. In certain embodiments there are at least 6, 7, 8, 9, 10, 11, or 1° different primer pairs in a PCR reaction. In some embodiments there are between 8 to 100, 8 to 80, 8 to 60, 8 to 40, 8 to 20, 8 to 18, 8 to 16, 8 to 12, 10 to 100, 10 to 80, 10 to 60, 10 to 40, 10 to 20, 10 to 18, 10 to 16, 10 to 12, 12 to 100, 12 to 80, 12 to 60, 12 to 40, 12 to 20, 12 to 18, or 12 to 16 different primer pairs in a PCR reaction. In certain embodiments there are at least 6, 7, 8, 9, 10, 11, or 12 different target nucleic acids in a PCR reaction. In some embodiments there are between 8 to 100, 8 to 80, 8 to 60, 8 to 40, 8 to 20, 8 to 18, 8 to 16, 8 to 12, 10 to 100, 10 to 80, 10 to 60, 10 to 40, 10 to 20, 10 to 18, 10 to 16, 10 to 12, 12 to 100, 12 to 80, 12 to 60, 12 to 40, 12 to 20, 12 to 18, or 12 to 16 different target nucleic acids in a PCR reaction.

Thus, one embodiment provides a multiplex method for amplifying one or more target nucleic acids comprising: (a) contacting a sample with a plurality of nucleic acid constructs as disclosed herein, wherein the target-specific primer regions of said plurality of nucleic acid constructs are configured as a plurality of primer pairs for amplifying a plurality of target nucleic acids; (b) hybridizing the plurality of target nucleic acid constructs to one or more target nucleic acid(s) if present in the sample; (c) cleaving the plurality of nucleic acid constructs that have hybridized to the target nucleic acid(s) with a cleaving agent that recognizes the target-binding dependent cleavage sequences of the plurality of nucleic acid constructs to obtain extendable primers; and (d) extending the extendable primers to amplify the target nucleic acid(s). Although these methods have been described with both primers of a primer pair being hairpin primers disclosed herein, these methods alternatively could be performed with only one primer of the primer pair is a hairpin primer and the other is a conventional linear primer.

In certain embodiments, the methods further comprise detecting the amplified target nucleic acid(s). The method of detection will depend on the manner in which the amplicons are labeled. For example, in embodiments where the nucleic acid construct comprises an extension blocker 5' of the target-specific primer region and 3' of the first stem forming region, resulting in a single-stranded tag region at the 5' of the amplified target nucleic acid, the detection may involve probing the tag with a complementary labeled probe or capturing the amplified target nucleic acid by hybridization of the tag region to a complementary nucleic acid immobilized on a solid support. Probes present in the PCR reaction may comprise a blocked 3' hydroxyl group to prevent extension of the probes by the polymerase. The 3' hydroxyl group may be blocked with, for example, a phosphate group or a 3' inverted dT. In other embodiments, a label or labels are incorporated into the amplicon by one or both of the primers. In certain embodiments, the amplicons may be labeled with a DNA binding dye like ethidium bromide or SYBR Green.

A labeling agent, which may also be referred to as a reporter, is a molecule that facilitates the detection of a molecule (e.g., a nucleic acid sequence) to which it is attached. Numerous reporter molecules that may be used to label nucleic acids are known. Direct reporter molecules include fluorophores, chromophores, and radiophores. Indirect reporter molecules include biotin, which must be bound to another molecule such as streptavidin-phycoerythrin for detection. Pairs of labels, such as fluorescence resonance energy transfer pairs or dye-quencher pairs, may also be employed. Labeled amplification products may be labeled directly or indirectly. Direct labeling may be achieved by, for example, using labeled primers, using labeled dNTPs, using labeled nucleic acid intercalating agents, or combinations of the above. Indirect labeling may be achieved by, for example, hybridizing a labeled probe to the amplification product.

A variety of solid supports for the immobilization of biomolecules are known. For example, the solid support may be nitrocellulose, nylon membrane, glass, activated quartz, activated glass, polyvinylidene difluoride (PVDF) membrane, polystyrene substrates, polyacrylamide-based substrate, other polymers, copolymers, or crosslinked polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules). A solid support may be in the form of, for example, a particle (e.g., a bead or microsphere), a column, or a chip. Molecules immobilized on planar solid supports are typically identified by their spatial position on the support. Molecules immobilized on non-planar solid supports, such as beads, are often identified by some form of encoding of the support. Particles may be encoded such that one subpopulation of particles can be distinguished from another subpopulation. Encoding may be by a variety of techniques. For example, the particles may be fluorescently labeled with fluorescent dyes having different emission spectra and/or different signal intensities. In certain embodiments, the particles are Luminex MicroPlex® or MagPlex® microspheres. The size of the particles in a subpopulation may also be used to distinguish one subpopulation from another. Another method of modifying a particles is to incorporate a magnetically responsive substance, such as Fe3O4, into the structure. For example, paramagnetic and superparamagnetic microspheres have negligible magnetism in the absence of a magnetic field, but application of a magnetic field induces alignment of the magnetic domains in the microspheres, resulting in attraction of the microspheres to the field source. Combining fluorescent dyes, particle size, and/or magnetically responsive substances into the particles (e.g., beads) can further increase the number of different subpopulations of particles that can be created.

In some embodiments, the amplified target nucleic acid(s) are detected or otherwise analyzed by melt analysis. In certain embodiments in which the nucleic acid constructs lack an extension blocker 5' of the target-specific primer region and 3' of the first stem forming region, the first stem forming region can be configured to provide a predetermined increase in the melting temperature of the amplified target nucleic acid as compared to the melting temperature of the amplified target nucleic acid without the first stem forming region. Distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein) can be used to, for example, identify or distinguish between two or more different target nucleic acids. Non-limiting examples of labeling agents suitable for melt analysis include intercalating agents, double-stranded DNA binding dyes, FRET pairs, or fluor/quencher pairs. In a particular embodiment, the melt analysis uses a fluor-labeled isobase (e.g., HEX or FAM labeled isoC) on one strand and a complementary quencher-labeled isobase on the other strand (e.g., dabcyl-labeled isoG).

In embodiments in which the nucleic acid constructs lack an extension blocker 5' of the target-specific primer region and 3' of the first stem forming region, the amplification methods disclosed herein may be performed such that initial stages are performed at a first temperature and later stages are performed at a second temperature, which is higher than the first. In this way, only the primers that have been copied through the first stem forming region can hybridize In another embodiment, there is provided a method of detecting a single nucleotide polymorphism comprising: (a) contacting a sample with at least a first and a second nucleic acid construct, each of the first and second nucleic acid constructs comprising: (a) a target-specific primer region; (b) a first stem forming region 5' of the target-specific primer region; and (c) a second stem forming region 3' of the target-specific primer region, wherein the second stem forming region is complementary to the first stem forming region; wherein the target-specific region of the first nucleic acid construct comprises a ribonucleotide complementary to a wildtype nucleotide in the target nucleic acid sequence, and the target-specific region of the second nucleic acid construct comprises a ribonucleotide complementary to a polymorphic nucleotide in the target nucleic acid sequence; (b) hybridizing the first and second nucleic acid constructs to the target nucleic acid if present in the sample; (c) cleaving any of the first and second nucleic acid constructs hybridized to the target nucleic acid with RNase H to create an extendable primer; (d) extending the extendable primers to amplify the target nucleic acid(s); and (e) detecting the presence or absence of the single nucleotide polymorphism by determining whether the amplified target nucleic acid(s) were amplified by one or both of the first and second target nucleic acid constructs. In certain aspects, the method further comprises contacting the sample with a primer configured to form a primer pair with both the first and second nucleic acid constructs (i.e., the allele specific constructs). This additional primer may be contacted with the sample as a linear primer or as a third nucleic acid construct comprising: (a) a target-specific primer region, wherein the target-specific region comprises a ribonucleotide; (b) a first stem forming region 5' of the target-specific primer region; and (c) a second stem forming region 3' of the target-specific primer region, wherein the second stem forming region is complementary to the first stem forming region.

The methods disclosed herein may further comprise quantifying the initial amount of the target nucleic acid(s) in the sample. The quantification may comprise, for example, determining the relative concentrations of DNA present during the exponential phase of the real-time PCR by plotting fluorescence against cycle number on a logarithmic scale. The amounts of DNA may then be determined by comparing the results to a standard curve produced by real-time PCR of serial dilutions of a known amount of DNA. Additionally, real-time PCR may be combined with reverse transcription polymerase chain reaction to quantify RNAs in a sample, including low abundance RNAs.

In certain embodiments, the methods disclosed herein may further comprise performing a reverse transcription (RT) reaction using one or more RT primers. Various embodiments of the present invention are particularly useful in "one-step RT/PCR" reactions where the reverse transcription step and PCR are performed in a single closed tube without stepwise addition of reagents. Conventional RT-PCR methods often use the same primers for RT and PCR. The RT and PCR steps are not typically performed at the same temperature however, as many RT enzymes are heat labile and most active at lower temperatures. Thus, the primers that are required to anneal at the higher annealing temperature of PCR may anneal non-specifically at the RT annealing temperature which is several degrees lower. The hairpin primers disclosed herein improve the specificity at these lower temperatures by providing primers that are blocked from forming non-specific hybridizations by the hairpin structure, in addition to comprising a specific cleavage domain. Embodiments are provided which allow two primers that are designed to anneal to the same target region to be used specifically for one-step RT-PCR reactions. One primer is designed with a lower $Tm_{specific}$ and is intended to act as the RT primer. The other primer is designed with a higher $Tm_{specific}$ and is intended to act as the PCR primer. The primer that has the higher $Tm_{specific}$ is blocked from annealing non-specifically during the RT stage by virtue of the hairpin formation. The primer with the lower $Tm_{specific}$, may or may not have a hairpin.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Hairpin Primers

Figure 1:
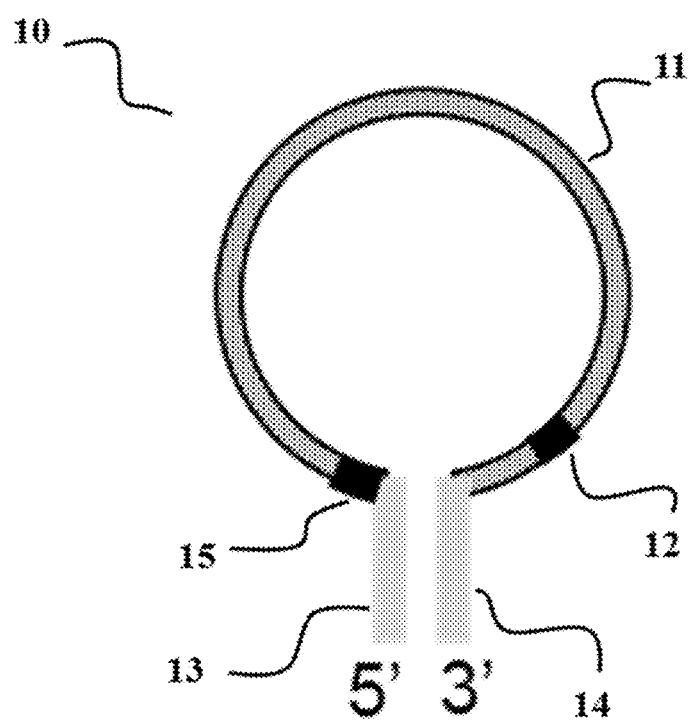
FIG. 1 is an illustration of one embodiment of a nucleic acid construct in a folded or hairpin state.

Various embodiments of the present invention provide nucleic acid constructs that assume a folded or "hairpin" state under certain conditions. FIG. 1 illustrates one embodiment in which a nucleic acid construct 10 comprises a target-specific primer region 11, which includes a target-binding dependent cleavage sequence 12. A first stem forming region 13 is located 5' of the target-specific primer region 11, and a second stem forming region 14 is located 3' of the target-specific primer region. First stem forming region 13 and second stem forming region 14 are complementary such that they hybridize and form the stem of the nucleic acid construct when it is in a hairpin state as shown in FIG. 1. In this embodiment, nucleic acid construct 10 includes polymerase extension blocker 15. Polymerase extension blocker 15 is located 5' of the target-specific primer region 11 and 3' of the first stem forming region 13. By inserting extension blocker 15 in front of (i.e., 3' of) first stem forming region 13, first stem forming region 13 is not incorporated into the amplicon. This would create a 5' single-stranded region or "tag" at one end of the amplicon, if only one of a pair of nucleic acid constructs used in the amplification has extension blocker 15, or on both ends of the amplicon if both nucleic acid constructs have the extension blocker 15.

Figure 2A:
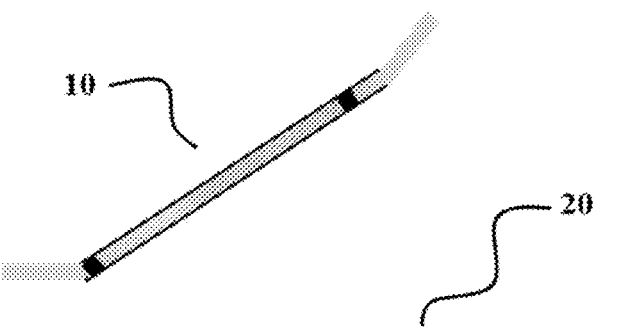
FIGS. 2A-2D illustrate embodiments in which a nucleic acid construct is in an unfolded state and not annealed to a target nucleic acid (FIG. 2A), an unfolded nucleic acid construct is annealed to a target nucleic acid (FIG. 2B), the nucleic acid construct has been cleaved resulting in a released fragment and a primer fragment, and the primer fragment has been extended (FIG. 2C), and nucleic acid constructs that are in the hairpin state (FIG. 2D).
Figure 2B:
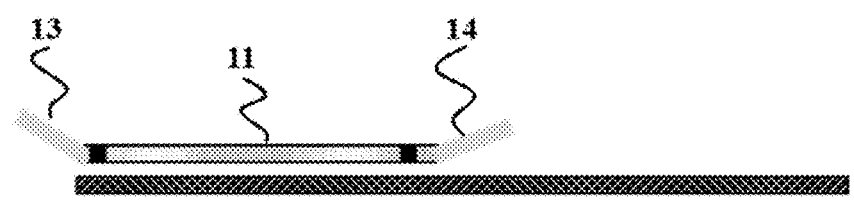
Figure 2C:
Figure 2D:
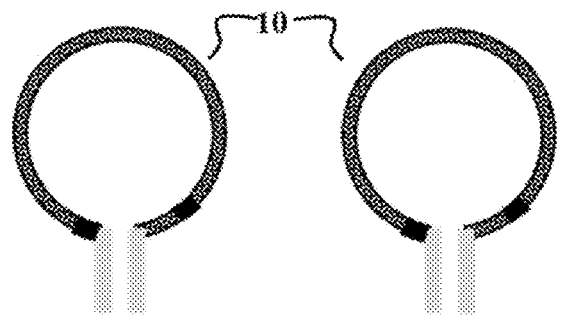

FIGS. 2A-2D illustrate an embodiment in which a nucleic acid construct is annealed to a target nucleic acid, cleaved to generate a cleaved fragment and a primer fragment, the primer fragment is extended using the target nucleic acid as the template. The melt temperature (Tm) of the folded state of nucleic acid construct 10, $Tm_{hairpin}$, is designed to be lower than the Tm of the target-specific region of the primer that is complementary to target nucleic acid 20, $Tm_{specific}$. Thus, as shown in FIG. 2A, when the temperature, T, is greater than $Tm_{specific}$, nucleic acid construct 10 is in an unfolded state and is not annealed to target nucleic acid 20. As the temperature is lowered from above $Tm_{specific}$ to below $Tm_{specific}$, unfolded nucleic acid construct 10 anneals to target nucleic acid 20 as shown in FIG. 2B. Also as shown in FIG. 2B, stem forming regions 13 and 14 are not complementary to target nucleic acid sequence 20. Once annealed to target nucleic acid sequence 20, the target-binding dependent cleavage sequence 12 is recognized by a cleaving agent and cleaved. Cleavage results in (1) a released fragment 16 containing the second stem forming region 14 and a portion of the target-specific region that is 3' of the cleavage site, and (2) a primer fragment 17. Released fragment 16 is designed to have a significantly lower melting temperature with target nucleic acid sequence 20 than does primer fragment 17, and will unanneal, allowing extension to occur from the now available 3' end of primer fragment 17 as shown in FIG. 2C. When the temperature is lowered below $Tm_{specific}$, and approaches $Tm_{hairpin}$, nucleic acid constructs 10 that did not anneal to the target nucleic acid sequence 20, and therefore were not cleaved, fold into the hairpin state as shown in FIG. 2D, making them unavailable for mispriming events at the lower temperatures.

As described above, a nucleic acid construct is designed to function as a "primer" under certain conditions. A "primer" is a short nucleic acid, usually a ssDNA oligonucleotide, which may be annealed to a target polynucleotide by complementary base-pairing. In certain embodiments, the primer has a target-specific sequence that is between 10-40, 15-30, or 18-26 nucleotides in length. The primer may then be extended along the target DNA or RNA strand by a polymerase enzyme, such as a DNA polymerase enzyme. Primer pairs can be used for amplification (and identification) of a nucleic acid sequence (e.g., by the polymerase chain reaction (PCR)). In certain embodiments, the nucleic acid constructs may contain one or more labels. Typical labels include fluorescent dyes, quenchers, radioactive isotopes, ligands, scintillation agents, chemiluminescent agents, and enzymes.

As used herein, "complementarity" describes the relationship between two single-stranded nucleic acid sequences that anneal by base-pairing. For example, 5'-AGT-3' pairs with its complement, 3'-TCA-5'. In some embodiments, primers or probes may be designed to include mismatches at various positions. As used herein, a "mismatch" means a nucleotide pair that does not include the standard Watson-Crick base pairs, or nucleotide pairs that do not preferentially form hydrogen bonds. The mismatch may include a natural nucleotide or a non-natural or non-standard nucleotide substituted across from a particular base or bases in a target. For example, the probe or primer sequence 5'-AGT-3' has a single mismatch with the target sequence 3'-ACA-5'. The 5' "A" of the probe or primer is mismatched with the 3' "A" of the target. Similarly, the target sequence 5'-AGA-3' has a single mismatch with the probe or primer sequence 3'-(iC)CT-5'. Here an iso-C is substituted in place of the natural "T." However, the sequence 3'-(iC)CT-5' is not mismatched with the sequence 5'-(iG)GA-3'.

An oligonucleotide that is specific for a target nucleic acid will "hybridize" to the target nucleic acid under suitable conditions. As used herein, "hybridization," "hybridizing," "anneal," or "annealing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions. Permissive conditions for annealing of nucleic acid sequences are routinely determinable by one of ordinary skill in the art. Stringency of hybridization may be expressed, in part, with reference to the temperature. The $T_m$ is the temperature (under defined ionic strength and pH) at which 50% of the target sequence hybridizes to a perfectly matched probe. Equations for calculating $T_m$, for example, nearest-neighbor parameters, and conditions for nucleic acid hybridization are known in the art.

As used herein, "nucleic acid," "nucleotide sequence," or "nucleic acid sequence" refer to a nucleotide, oligonucleotide, polynucleotide, or any fragment thereof and to naturally occurring or synthetic molecules. These terms also refer to DNA or RNA of genomic or synthetic origin, which may be single-stranded or double-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. RNA may be used in the methods described herein and/or may be converted to cDNA by reverse transcription for use in the methods described herein.

II. Cleaving Agents

The target-specific region of various embodiments of the hairpin primers disclosed herein include a target-binding dependent cleavage sequence. The target-binding dependent cleavage sequence is a sequence that is recognized by a cleaving agent when in a double-stranded state but is not recognized to a significant degree by the cleaving agent when in a single-stranded state. In the hairpin state of the nucleic acid constructs described herein, the target-specific region is single stranded and, therefore, it is not a substrate for the cleaving agent. When the nucleic acid construct is hybridized to a target nucleic acid, the target-binding dependent cleavage sequence is double stranded and, therefore, is a substrate for the cleaving agent.

In certain embodiments the target-binding dependent cleavage sequence may comprise one or more ribonucleotides and the cleaving agent may be an RNase, such as RNase H, RNase H2, RNase H2A, RNase H2B, and RNase H2C, and hotstart and/or thermophilic variants thereof. RNase H and RNase H2 are non-specific endonucleases and catalyze the cleavage of RNA in a RNA/DNA duplex, and members of the RNase H family can be found in nearly all organisms. RNase H preferentially cleaves the 3'-O—P- bond of RNA, generating 3' hydroxyl and 5' phosphate products. RNase H2 preferentially nicks 5' to a ribonucleotide within the context of a DNA duplex, leaving 5' phosphate and 3' hydroxyl ends.

In other embodiments the target-binding dependent cleavage sequence may comprise sequence-specific nicking enzyme recognition sequence and the cleaving agent may be a sequence-specific nicking enzyme. Sequence-specific nicking enzymes hydrolyze only one strand of DNA, and they do so in a sequence-specific, strand-specific, and location-specific manner. Thus, unlike certain restriction endonucleases that hydrolyze both strands of duplex DNA ("cleave"), sequence-specific nicking enzymes hydrolyze only one strand of duplex DNA ("nick"). The nicks introduced into DNA by the actions of these enzymes can serve as initiation points for further enzymatic reactions including polymerization. Examples of sequence-specific nicking enzymes include BbvCl and AlwI. Examples of sequence-specific nicking enzymes are also disclosed in, for example, U.S. Pat. No. 7,081,358, which is incorporated herein by reference.

III. PCR

The nucleic acid constructs disclosed herein are particularly useful in single-plex PCR, multiplex PCR, and RT-PCR, because these constructs are configured such that they are closed (i.e., in a hairpin state), and thus unavailable for mispriming or primer-dimer formation at temperatures lower than the specific annealing temperature of the target-specific sequence to the target sequence, which significantly mitigates non-specific interactions. As used herein, "amplification" or "amplifying" refers to the production of additional copies of a nucleic acid sequence. The term "amplification reaction mixture" refers to an aqueous solution comprising the various reagents used to amplify a target nucleic acid. These may include enzymes (e.g., a thermostable polymerase), aqueous buffers, salts, amplification primers, target nucleic acid, nucleoside triphosphates, and optionally, at least one labeled probe and/or optionally, at least one agent for determining the melting temperature of an amplified target nucleic acid (e.g., a fluorescent intercalating agent that exhibits a change in fluorescence in the presence of double-stranded nucleic acid).

The polymerase chain reaction (PCR) is a technique widely used in molecular biology to amplify a piece of DNA by in vitro enzymatic replication. Typically, PCR applications employ a heat-stable DNA polymerase, such as Taq polymerase. This DNA polymerase enzymatically assembles a new DNA strand from nucleotides (dNTPs) using single-stranded DNA as template and DNA primers to initiate DNA synthesis. A basic PCR reaction requires several components and reagents including: a DNA template that contains the target sequence to be amplified; one or more primers, which are complementary to the DNA regions at the 5' and 3' ends of the target sequence; a DNA polymerase (e.g., Taq polymerase) that preferably has a temperature optimum at around 70° C.; deoxynucleotide triphosphates (dNTPs); a buffer solution providing a suitable chemical environment for optimum activity and stability of the DNA polymerase; divalent cations, typically magnesium ions ($Mg2^+$); and monovalent cation potassium ions. A reverse transcriptase PCR (RT-PCR) amplification procedure may be performed to reverse transcribe mRNA into cDNA. Methods of RT-PCR are well known in the art (see Sambrook et al., 2001).

The majority of PCR methods use thermal cycling to subject the PCR sample to a defined series of temperature steps. Each cycle typically has 2 or 3 discrete temperature steps. The cycling is often preceded by a single temperature step ("initiation") at a high temperature (>90° C.), and followed by one or two temperature steps at the end for final product extension ("final extension") or brief storage ("final hold"). The temperatures used and the length of time they are applied in each cycle depend on a variety of parameters. These include the enzyme used for DNA synthesis, the concentration of divalent ions and dNTPs in the reaction, and the melting temperature (Tm) of the primers. Commonly used temperatures for the various steps in PCR methods are: initialization step—94-96° C.; denaturation step—94-98° C.; annealing step—50-65° C.; extension/elongation step—70-74° C.; final elongation—70-74° C.; final hold—4-10° C.

Real-time polymerase chain reaction, also called quantitative real time polymerase chain reaction (qPCR) or kinetic polymerase chain reaction, is used to amplify and simultaneously detect, and optionally quantify, a targeted DNA molecule. It enables both detection and quantification (as absolute number of copies or relative amount when normalized to DNA input or additional normalizing genes) of a specific sequence in a DNA sample. Real-time PCR may be combined with reverse transcription polymerase chain reaction to quantify low abundance RNAs. Relative concentrations of DNA present during the exponential phase of real-time PCR are determined by plotting fluorescence against cycle number on a logarithmic scale. Amounts of DNA may then be determined by comparing the results to a standard curve produced by real-time PCR of serial dilutions of a known amount of DNA. Various PCR and real-time PCR methods are disclosed in U.S. Pat. Nos. 5,656,493; 5,994,056; 6,174,670; 5,716,784; 6,030,787; 6,174,670, and 7,955,802, which are incorporated herein by reference.

In qPCR the threshold cycle (Ct) reflects the cycle number at which the fluorescence generated within a reaction crosses the threshold. It is inversely correlated to the logarithm of the initial copy number. The determination of the Ct value for each reaction may be related to the baseline, background, and threshold set by software. In some qPCR methods, a passive reference dye is used and the signal from the fluorescent reporter is divided by the signal from the reference dye to account for variability in the reaction medium. This calculation gives the normalized reporter signal (Rn). The baseline refers to the initial cycles in PCR in which there is little expected change in fluorescent signal (usually cycles 3 to 15). This baseline can be used to determine the background for each reaction. In a multiwell reaction plate, several baselines from multiple wells may be used to determine the 'baseline fluorescence' across the plate. There are many ways to use data analysis to determine when target amplification is above the background signal (crosses the threshold). Rn can be subtracted by the background signal to give ΔRn. Other supplements to data analysis that are typically employed in qPCR may be applied to the present invention. Namely, the use of endogenous and exogenous controls, housekeeping genes, standard curves, internal positive controls, no amplification controls, reverse transcription controls, nontreated controls, extraction controls, time point zeros, healthy individual controls, and negative and positive controls. These may be used in the present invention in order to perform Comparative Ct analysis ("relative quantitation") or standard curve analysis ("absolute quantitation"), the Pfaffl method, end-point quantitation, qualitative results, allelic discrimination, etc. Accounting for amplification efficiency or amplification rate may be performed by a number of methods including but not limited to: Dilution method, fluorescence increase in exponential phase, Sigmoidal or logistic curve fit, etc. The threshold may be determined by a number of methods including but not limited to the second derivative maximum method, or by a multiple of standard deviations above background, etc. Endpoint quantitative analysis could be performed by a number of methods including but not limited to: relative, absolute, competitive and comparative.

Digital PCR (dPCR) involves partitioning the sample such that individual nucleic acid molecules contained in the sample are localized in many separate regions, such as in individual wells in microwell plates, in the dispersed phase of an emulsion, or arrays of nucleic acid binding surfaces. Each partition will contain 0 or 1 molecule, providing a negative or positive reaction, respectively. Unlike conventional PCR, dPCR is not dependent on the number of amplification cycles to determine the initial amount of the target nucleic acid in the sample. Accordingly, dPCR eliminates the reliance on exponential data to quantify target nucleic acids and provides absolute quantification.

Multiplex-PCR and multiplex real-time PCR use of multiple, unique primer sets within a single PCR reaction to produce amplicons of different DNA sequences. By targeting multiple genes at once, additional information may be gained from a single test run that otherwise would require several times the reagents and more time to perform. Annealing temperatures for each of the primer sets should be optimized to work within a single reaction.

Approaches such as allele-specific PCR (AS-PCR) and allele-specific primer extension (ASPE) detect mutations and polymorphisms using oligonucleotide primers selected such that they selectively achieve primer extension of either a sequence containing a variant nucleotide or the corresponding sequence containing the wild-type nucleotide. Such approaches are described in, for example, U.S. Pat. Nos. 5,595,890, 5,639,611, and 5,137,806, the disclosures of which are incorporated by reference. An allele-specific primer has a discriminating nucleotide. The discriminating nucleotide may be at the 3' terminus of the primer or it may be internal (i.e., not at the 3' terminus). In certain embodiments the internal, allele-discriminating nucleotide is at the 3' terminus of the primer fragment, in other embodiments it is at the second, third, fourth, or fifth nucleotide from the 3' terminus of the primer fragment.

IV. Isothermal Amplification

While the hairpin primers disclosed herein are useful in PCR performed on a thermal cycler over a range of temperatures, they can also benefit isothermal amplification techniques. Isothermal amplification techniques such as helicase-dependent amplification, nicking-enzyme amplification (NEAR) (see, e.g., WO 96/23904, incorporated herein by reference), and recombinase polymerase amplification (RPA), allow for amplification of the target nucleotide (s) at a single fixed temperature. Nevertheless, variations in set annealing temperature between instruments or platforms can still be a problem, particularly in point-of-care type of devices. Assays performed on these devices can benefit from the hairpin primers described herein.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. Nos. 5,137,806, 5,432,272, 5,595,890, 5,639,611, 5,656,493; 5,716,784, 5,994,056, 5,773,258 5,677,152, 5,338,671, 6,030,787, 6,174,670, 6,977,161, 7,081,358, 7,226,737, 7,955,802, 7,422,850, and 8,624,014

U.S. Patent Publication Nos. 2012/0258455 and US2013/0288245
International (PCT) Patent Publication No. WO 96/23904
Kaboev et. al. *Nucleic Acids Research*, Vol. 28, No. 21 e94, 2000
Sambrook et al., 2001

What is claimed is:

1. A method for amplifying a target nucleic acid comprising:
   (a) contacting a sample with a first nucleic acid construct and a second nucleic acid construct, each of said first and second nucleic acid constructs comprising (i) a target-specific primer region, wherein the target-specific region comprises a target-binding dependent cleavage sequence; (ii) a first stem forming region 5' of the target-specific primer region; and (iii) a second stem forming region 3' of the target-specific primer region, wherein the second stem forming region is complementary to the first stem forming region, wherein the target-specific primer regions of said first and second nucleic acid constructs are configured as a primer pair for amplifying a target nucleic acid;
   (b) hybridizing the first and second nucleic acid constructs to the target nucleic acid if present in the sample;
   (c) cleaving the first and second nucleic acid constructs with a cleaving agent that recognizes the target-binding dependent cleavage sequences of the first and second nucleic acid constructs to obtain first and second extendable primers; and
   (d) extending the first and second extendable primers to amplify the target nucleic acid.

2. The method of claim 1, wherein the target-binding dependent cleavage sequences comprise a ribonucleotide and the cleavage agent is an RNase H2.

3. The method of claim 1, further comprising performing a melt analysis on the amplified target nucleic acid(s).

4. The method of claim 3, wherein the nucleic acid constructs lack an extension blocker 5' of the target-specific primer region and 3' of the first stem forming region, and further wherein the first stem forming region is configured to provide a predetermined increase in the melting temperature of the amplified target nucleic acid as compared to the melting temperature of the amplified target nucleic acid without the first stem forming region.

5. The method of claim 1, wherein the nucleic acid constructs comprises an extension blocker 5' of the target-specific primer region and 3' of the first stem forming region, resulting in a single-stranded tag region at the 5' of the amplified target nucleic acid.

6. The method of claim 5, further comprising capturing the amplified target nucleic acid by hybridization of the tag region to a complementary nucleic acid immobilized on a solid support.

7. A method of detecting a single nucleotide polymorphism comprising:
   (a) contacting a sample with at least a first and a second nucleic acid construct, each of the first and second nucleic acid constructs comprising:
      (a) a target-specific primer region;
      (b) a first stem forming region 5' of the target-specific primer region; and
      (c) a second stem forming region 3' of the target-specific primer region, wherein the second stem forming region is complementary to the first stem forming region;
      wherein the target-specific region of the first nucleic acid construct comprises a ribonucleotide complementary to a wildtype nucleotide in the target nucleic acid sequence, and the target-specific region of the second nucleic acid construct comprises a ribonucleotide complementary to a polymorphic nucleotide in the target nucleic acid sequence;
   (b) hybridizing the first and second nucleic acid constructs to the target nucleic acid if present in the sample;
   (c) cleaving any of the first and second nucleic acid constructs hybridized to the target nucleic acid with RNase H to create an extendable primer;
   (d) extending the extendable primers to amplify the target nucleic acid(s); and
   (e) detecting the presence or absence of the single nucleotide polymorphism by determining whether the amplified target nucleic acid(s) were amplified by one or both of the first and second target nucleic acid constructs.

8. The method of claim 7, wherein the first and second nucleic acid constructions have different fluorescent labels, and determining whether the amplified target nucleic acid(s) were amplified by one or both of the first and second target nucleic acid constructs comprises fluorescence detection.

9. The method of claim 7, wherein the first and second nucleic acid constructions have different first stem forming regions, and determining whether the amplified target nucleic acid(s) were amplified by one or both of the first and second target nucleic acid constructs comprises melt analysis.

10. The method of claim 7, wherein the first and second nucleic acid constructions have different first stem forming regions and an extension blocker 3' of the different first stem forming regions, and determining whether the amplified target nucleic acid(s) were amplified by one or both of the first and second target nucleic acid constructs comprises capturing the amplified target nucleic acid(s) on one or more solid supports.

* * * * *